United States Patent [19]

Saito et al.

[11] Patent Number: 4,605,670

[45] Date of Patent: Aug. 12, 1986

[54] METHOD FOR PERCUTANEOUSLY ADMINISTERING METOCLOPRAMIDE

[75] Inventors: Kenichiro Saito, Menlo Park; Jorge Heller, Woodside; Wilfred A. Skinner, Portla Valley, all of Calif.

[73] Assignee: Nitto Electric Industrial Co., Ltd., Osaka, Japan

[21] Appl. No.: 576,087

[22] Filed: Feb. 1, 1984

[51] Int. Cl.⁴ .................. A61K 31/165; A61K 47/00
[52] U.S. Cl. .................................... 514/619; 514/785; 514/969; 604/290; 604/304; 604/896
[58] Field of Search ................ 604/896, 290, 304; 514/785, 788, 619, 947, 969

[56] References Cited

U.S. PATENT DOCUMENTS 3,964,482  6/1976  Gerstel et al. ............... 604/896
4,411,893 10/1983  Johnson et al. .............. 514/947
4,444,762  4/1984  Rajadhyaksha ............... 514/947

FOREIGN PATENT DOCUMENTS 043738   7/1981  European Pat. Off. .
069385   7/1982  European Pat. Off. .
2001768 10/1969  France .
57-134413 8/1982 Japan .
WO83/01000 3/1983 PCT Int'l Appl. ............ 514/785

Primary Examiner—Howard S. Williams
Attorney, Agent, or Firm—Sughrue, Mion, Zinn, Macpeak, and Seas

[57] ABSTRACT

A method of percutaneously administering metoclopramide which comprises applying to the skin of a mammal metoclopramide in a carrier system which comprises at least one adjuvant and at least one solvent. The adjuvant is a monovalent alcohol ester of an aliphatic monocarboxylic acid or an aliphatic monoalcohol. The solvent is a pyrrolidone-type compound. Mixtures can also be used.

10 Claims, 1 Drawing Figure

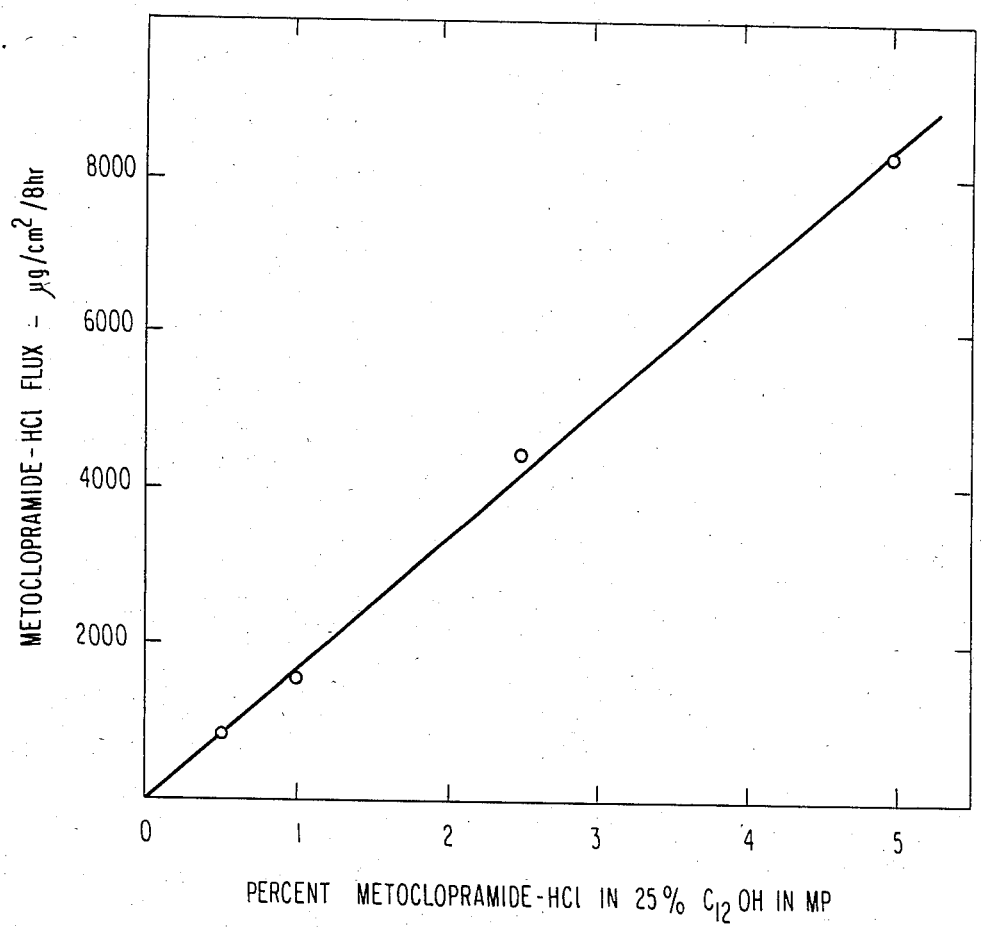

METHOD FOR PERCUTANEOUSLY ADMINISTERING METOCLOPRAMIDE

BACKGROUND OF THE INVENTION

1. Field of the Invention

The present invention relates to a method for accelerating the percutaneous absorption of metoclopramide (hereafter often merely MCP for brevity).

2. Description of the Prior Art

Drugs are commonly administered to the skin or mucosal tissues to treat local problems and systemic administration of drugs is commonly accomplished by ingesting pills or by injections. However, recently attempts have been made to achieve systemic administration of drugs by topical applications to the skin or mucosal tissues. Such topical means of achieving systemic administration has the advantage that desired blood levels can be readily achieved and maintained so that duration of therapy can be readily controlled. Thus, side effects due to an overdose of the drug can be prevented. Also, metabolism due to a first pass through the liver and gastric disturbances, which are characteristic of certain drugs such as indomethacin when administered orally, can also be eliminated.

However, normal skin is relatively impermeable to most drugs in that desired blood levels of the therapeutic agent cannot be achieved by means of percutaneous absorption. The percutaneous absorption of drugs can, however, be enhanced by means of adjuvants or penetration enhancers.

One of the best known of such penetrating adjuvants is dimethyl sulfoxide, the use of which is described in detail in U.S. Pat. No. 3,551,554 Herschler et al.

British Pat. No. 1,504,302 Brooker et al deals with sedative methods and compositions and discloses the administration of sedatives by applying to the skin of a non-human animal a sedating amount of one or more sedative compounds in various penetrating adjuvants such as hydrocarbons such as aromatic hydrocarbons or paraffins, halogenated aliphatic hydrocarbons, ketones, esters, ethers, alcohols, amides or sulfones.

U.S. Pat. No. 4,202,888 Eckert et al discloses absorbable pharmaceutical compositions comprising at least one cardiac glycoside distributed in a vehicle comprising an absorption-enhancing amount of at least a partial glyceride of a fatty acid of medium chain length.

U.S. Pat. No. 3,472,931 Stoughton relates to percutaneous absorption using lower alkyl amides, and exemplifies binary systems which comprise dimethylacetamide and ethanol, dimethyl acetamide and isopropyl alcohol and dimethylacetamide and isopropyl palmitate.

U.S. Pat. No. 3,969,516 Stoughton discloses compositions for the treatment of acne which broadly can include "conventional formulating ingredients" including materials which enhance the percutaneous absorption of antibiotics of the lincomycin family, e.g., N-lower alkyl 2-pyrrolidones. Stearyl alcohol is used in the examples. This is a solid at 38° C. and would be inoperable in the present inventions.

U.S. Pat. No. 3,989,816 Rajadhyakshn discloses percutaneous absorption systems for pyrrolidone-type compounds, including, e.g., in Example 3 isopropyl myristate without any disclosure of the purpose thereof. While stearyl and cetyl alcohol are disclosed, these are solids at 38° C. and are inoperable in the present invention. Further, the pyrrolidone-type compounds used in the examples have a $C_8$ group corresponding to $R_5$ of the solvents of the present invention which renders such useless in the present invention.

U.S. Pat. No. 4,017,641 DiGiulio discloses skin moisturizing compositions (emulsions) containing 2-pyrrolidinone. Stearyl and cetyl alcohol (solids at 38° C.) are disclosed as useful components. DiGiulio also broadly discloses the use of certain esters of lanolin fatty acids, certain straight chain fatty alcohols or straight chain fatty alcohols.

European Patent Application 0043738 discloses binary percutaneous administration systems which comprise a monoglyceride, a diol or a diol ether in combination with a second component such as an alcohol, ester, amide or the like.

The present invention involves multicomponent carrier systems for the percutaneous administration of metoclopramide which differ from the systems disclosed in the above prior art.

SUMMARY OF THE INVENTION

Per the present invention, it has been discovered that certain adjuvant-solvent systems provide enhanced and controlled percutaneous administration of metoclopramide (free base) and/or pharmaceutically acceptable salts thereof.

We consider the pyrrolidone-type compounds to basically serve a solvent function and the esters and/or alcohols to serve as adjuvants which enhance the solvating function of the solvent. We further believe that the solvents carry the active agent whereas the adjuvants open up the stratum corneum. We do not wish to be bound by these theories, and we merely use the terminology "solvent" and "adjuvant" to maintain a line of distinction between the two classes of materials which are mandatorily used in combination.

The adjuvants of the present invention are selected from $C_8$ to $C_{32}$ monovalent alcohol esters of aliphatic monocarboxylic acids and $C_6$ to $C_{24}$ aliphatic monoalcohols. The solvents are pyrrolidone-type compounds. Mixtures of such esters and alcohols may also be used as may mixtures of the pyrrolidone-type compounds. It is necessary that the alcohols, esters and pyrrolidone-type compounds of the present invention have a melting point below 38° C., i.e., be liquid at 38° C. Of course, the final compositions of the present invention which are used for percutaneous administration must also be liquid at below 38° C.

Per the present invention, metoclopramide can be percutaneously administered by blending the same with the adjuvant(s) and solvent(s) and applying the same to the skin.

If desired, a $C_3$ to $C_6$ diol moderator can be added to control (moderate) the rate of percutaneous metoclopramide administration.

The above described compositions can be used as bases for medical preparations comprising active agents applicable to the outer skin.

One object of the present invention is to provide base compositions or percutaneous absorption enhancing compositions, optionally with a diol moderator, for medical preparations for external use which enhance the permeability of metoclopramide through the skin and the percutaneous absorption of metoclopramide.

Another object of the present invention is to provide a method for enhancing the permeability of metoclopramide through the skin percutaneous absorption of metoclopramide.

Yet another object of the present invention is to provide compositions which ensure the rapid and controlled transepidermal delivery of metoclopramide in man or other animals.

Another object of the present invention is to provide such rapid and controlled transepidermal delivery which provides metoclopramide blood levels in the therapeutic range for the treatment of humans and other animals.

Still another object of the present invention is to provide, through transepidermal delivery, at appropriately adjusted rates, relatively constant therapeutic blood levels of metoclopramide so as to avoid the side effects and reduced therapeutic effects that may result from wide fluctuations in blood levels over time.

BRIEF DESCRIPTION OF THE DRAWING

The FIGURE shows the effect of increasing the concentration of metoclopramide.HCl in a 25% 1-dodecanol in 1-methyl-2-pyrrolidone system on metoclopramide flux.

DESCRIPTION OF PREFERRED EMBODIMENTS

Adjuvants include the following compounds. Monovalent alcohol esters of aliphatic monocarboxylic acids having a total number of carbon atoms of from 8 to 32. Diesters do not provide the results of the present invention.

The esters are conveniently represented by the formula $R_1COOR_2$, $R_1$ representing the acid moiety and $R_2$ representing the alcohol moiety. The total number of carbon atoms in $R_1$ and $R_2$ can be from 7 to 31.

As the alcohol moiety, monovalent alcohols having 1 to 20 carbon atoms such as methyl alcohol, ethyl alcohol, n-propyl alcohol, isopropyl alcohol, n-butyl alcohol, iso-butyl alcohol, decyl alcohol, tetradecyl alcohol and oleyl alcohol are preferred. Further, as the monocarboxylic acid moiety, fatty acids having 2 to 20 carbon atoms are preferred and fatty acids having 2 or 8 to 18 carbon atoms are most preferred. Specific examples of such esters include methyl laurate, ethyl laurate, butyl laurate, isopropyl myristate, decyl oleate, myristyl acetate, cetyl acetate, etc.

If the carboxylic acid moiety in the ester has 18 or more carbon atoms, the alcohol and/or carboxylic acid moiety must have at least one unsaturated bond and/or at least one branched chain to render the same liquid. In this situation it is preferred that the alcohol moiety have at least two carbon atoms, preferably more than two carbon atoms.

The presence of only one unsaturated bond is sufficient; the maximum number of unsaturated bonds is not limited. Similarly, the presence of only one branched methyl group is sufficient; the maximum number of carbon atoms in the branch(es) is not limited.

Higher aliphatic monoalcohols having from 6 to 24 carbon atoms which may be branched, straight chain, saturated or unsaturated and may be primary, secondary or tertiary.

If the alcohol has 14 or more carbon atoms, it must contain at least one unsaturated bond and/or at least one branched chain to render the same liquid. The presence of only one unsaturated bond is sufficient; the maximum number unsaturated bonds is not limited. Similarly, the presence of only one branched methyl group is sufficient; the maximum number of carbon atoms in the branch(es) is not limited.

The solvents are compounds represented by the general formula:

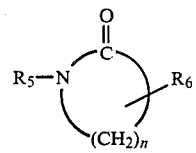

wherein $R_5$ represents a hydrogen atom or a lower alkyl group having 1 to 4 carbon atoms (methyl, ethyl, n-propyl, iso-propyl, etc.), $R_6$ represents a lower alkyl group with 1 to 4 carbon atoms which may be straight chain or branched (examples are as for $R_5$) and n represents an integer of 3 to 5. It is preferred that n be 3 or 4, and it is most preferred that n be 3 since unexpectedly superior results are achieved (see Example 2).

Specific examples thereof include 2-pyrrolidone, N-methylpyrrolidone, N-methylpiperidone, caprolactam, N-methylcaprolactam, etc.

It is mandatory that the adjuvant(s) and solvent(s) per the present invention both be present to achieve the synergistic effects of the present invention, as established by Example 8 herein.

As earlier indicated, a diol moderator may be used per the present invention. The diol can be straight or branched chain and the diol selected is preferably a diol comprising 3 to 6 carbon atoms.

The amount of diol moderator used is not unduly limited, but is typically on the order of about 10 to about 400 weight percent, more preferably about 25 to about 200 weight percent, based on the weight of the solvent. The resulting combination of materials must, of course, be liquid.

The diol moderator reduces the activity of the adjuvant of the present invention which provides a means of further controlling the rate of active agent absorption.

Greater amounts of diol moderator decrease the rate of metoclopramide flux while lesser amounts of diol moderator increase the rate of metoclopramide flux as compared to greater amounts.

It is to be understood that the diol moderator does not enhance percutaneous absorption per the present invention, rather, in all amounts it reduces the rate of percutaneous absorption, which effect has not been suspected in the art.

The compositions of the present invention may be prepared by dissolving the metoclopramide in the adjuvant or solvent or mixture thereof and then mixing the diol moderator therein if it is used. The order of mixing is not important. The amount of adjuvant used is generally from 0.5 to 95% by weight based on the total weight of adjuvant plus solvent plus metoclopramide, preferably 1 to 90% by weight same basis, the amount of solvent used being, accordingly, from 99.5 to 5% by weight, preferably 99 to 10% by weight, same basis. Preferred proportions of diol moderator have earlier been given. Of course, pharmaceutically acceptable additives such as water, etc., can also be added to the base compositions.

The amount of metoclopramide blended is sufficient if it is effective for achieving the desired pharmaceutical effect, which varies depending upon the body weight of the patient, symptoms, etc. The amount may thus be suitably chosen depending upon these conditions. In general, it is preferred that metoclopramide be employed in an amount of 0.1 to 60% by weight, more preferably 0.5 to 35% by weight, based on the weight of adjuvant plus solvent.

The dose of the metoclopramide administered can be controlled by increasing or decreasing the area of skin to which the pharmaceutical compositions are applied. Accordingly, the amount thereof is not necessarily limited to the above described amounts.

As will be apparent to one skilled in the art, with increasing concentrations of metoclopramide increasing amounts of the same will be absorbed by the subject. The following discussion is given in terms of blood levels of drug (ng/ml of plasma), this being dependent upon the total area of dermal application, as there is a substantially linear increase in amount of active agent absorbed with area.

For a constant area of application and a constant absolute amount of adjuvent, the blood level of metoclopramide at any given time is a function of the concentration of the same in the composition. That is, increased concentrations of metoclopramide in the formulation result in more rapid metoclopramide penetration and higher blood levels.

A further factor which must be considered is that the amount of metoclopramide absorbed will depend on the site of application, for example, scalp, ventral forearm, behind the ear, chest, etc. Typically an area rich in blood vessels is selected.

For most applications, the amount of metoclopramide applied will be about 0.1 mg to 100 mg per $cm^2$ and the total area of application will be on the order of about 0.5 $cm^2$ to about 100 $cm^2$, which will provide therapeutic blood levels of the metoclopramide.

These ranges are not, however, to be considered as limitative.

In general, the rate of transepidermal metoclopramide absorption will approach the rate of oral absorption depending upon the factors previously discussed (nature and amount of adjuvant and solvent, concentration of metoclopramide in the formulation, and surface area of skin application). Thus, peak blood levels of the metoclopramide may be reached more slowly or at about the same rate and will reach about the same level as those obtained by oral administration. Alternatively, the blood level of metoclopramide attained by single dose intravenous administration may be maintained for an extended period by subsequent percutaneous administration of the metoclopramide. In the latter case, the initial i.v. dose may be smaller than the normal therapeutic i.v. dose so that side effects associated with higher-than-minimal therapeutic blood levels attained by a reduced i.v. dose may be maintained by the subsequent transepidermal administration at a proper rate.

The method of the present invention finds application with mammals in general, most particularly man and domestic animals such as cows, sheep, horses, dogs, cats and the like.

The pharmaceutical composition of the present invention is administered to the outer skin as a simple mixture or as a medical preparation by adding known pharmaceutically acceptable third components in the form of solutions, ointments (paste-including creams and gels), lotions, adhesive tapes, a plaster, etc.

For example, solutions may simply comprise metoclopramide agent dissolved in the adjuvant and solvent with optional components, e.g., glycerin, etc., and the solutions may be incorporated into absorbents, e.g., a gauze, porous membrane, etc.

Ointments, gels or creams may contain conventional ingredients (e.g., polyethylene oxide) to form the same, and the same may be spread onto backing materials, e.g., a plastic film.

Similarly, plasters or adhesives tapes may contain the metoclopramide, adjuvent and solvent in an adhesive base, e.g., acrylic copolymers or other synthetic gums.

In a further preferred form of the invention a cellulosic gelling agent is present, typically a hydroxyalkylcellulose, e.g., hydroxyethylcellulose, hydroxypropylcellulose, hydroxypropylmethylcellulose, etc., generally in an amount of 1 to 10 wt % based on the weight of adjuvant plus solvent. The resulting gel is conveniently carried on a support.

The above listed components should essentially be inert in the system and not increase the effect of the adjuvant.

In developing the present invention, we used both diffusion cells and an animal model. The diffusion cell methods provided a qualitative assessment of the metoclopramide/adjuvant effect on percutaneous absorption. The animal model rhesus monkey test also provides an acceptable pharmacokinetic model for man as indicated in J. Soc. Cosmet. Chem., 30, 297–307. Sept./Oct. 1979 and Toxicol. Appl. Pharmacol., 32, 394–398, 1975.

Hereafter, metoclopramide is generally referred to as "MCP". Examples of useful pharmaceutically acceptable salts include the HCl or di HCl salts, etc.

EXPERIMENTAL

In Vitro Skin Penetration Studies with Diffusion Cell Technique

Rat full thickness skins were used in the diffusion cell method of Michaels, AIChE Journal, 21 [5], 985–996, (1975). The rat skin was mounted in the diffusion cell in a vertical position between the upstream and the downstream compartments; the exposed area of the skin approximated 4.15 $cm^2$.

The skin was excised from the shaved abdominal site of male albino rats weighing 250~300 g, and washed with normal saline solution after the subcutaneous fat was carefully removed with scissors.

An MCP solution of known concentration was added to the upper compartment of the cell, which was exposed to the epithelial side of the skin and a normal saline solution was placed in the lower compartment.

The penetration rate was studied in a thermostated bath at 30° C. At appropriate intervals samples were withdrawn from the lower compartment and subsequently analyzed for MCP concentration by standard analytical methods. This regimen was used in Examples 1 to 10.

In Vivo Rhesus Monkey Test

Male rhesus monkeys weighting 8–14 Kg were used as the subject. An appropriate area of the monkey's chest was shaved 24 hours before drug application.

MCP.HCl formulations were applied to a certain area of the chest. The monkey was restrained in a chair to prevent it from touching its chest.

Blood samples were taken at appropriate intervals after the application. The heparinized blood was centrifuged, and the plasma removed and stored at −20° C. until analyzed.

MCP was analyzed following the HPLC method of Graffner, Lagerstrom, and Lundborg, Br. J. Clin. Pharmac. 8, 469-474 (1979). The results are set forth in the following examples. This test was used in Examples 12 to 15 and MCP was analyzed per the Graffner et al method in control Example 11.

Further, in the following examples, the abbreviations below are used:

$C_{12}OH$—1-dodecanol
MP—1-methyl-2-pyrrolidone
PG—1,2-propanediol

Unless otherwise indicated, in all of the examples, the active agent was MCP.HCl, the MCP.HCl flux is given in terms of $ug/cm^2/8hrs$, 25 volume percent of the adjuvant with respect to the adjuvant plus solvent volume was used in combination with 2.5 weight percent of active agent based on the weight of the adjuvant plus solvent; otherwise, all percents are volume percents based on adjuvant, solvent or adjuvant plus solvent volume, depending on the system.

Compositions were typically prepared by merely mixing the adjuvant and solvent together, then mixing the MCP.HCl in the mixture and then, if used, mixing the diol therein. The order of mixing is not important.

EXAMPLE 1

This example shows the flux of MCP.HCl with combinations of various alcohols and 1-methyl-2-pyrrolidone.

| Alcohol | MCP HCl Flux$(ug/cm^2/8\ hrs)$ |
| --- | --- |
| 1-Octanol | 3834 |
| 4-Octanol | 3176 |
| Linalol | 4066 |
| Dragosantol | 2163 |
| 1-Dodecanol | 4552 |
| Oleyl Alcohol | 3287 |
| 2-Octyl-1-Dodecanol | 2176 |
| Phytol | 3040 |
| 2-Decyl-1-Tetradecanol | 1410 |

EXAMPLE 2

This example shows the use of 1-dodecanol as the adjuvant in combination with various pyrrolidone-type compounds as solvents. MCP.HCl was used as the active agent.

| Combination | MCP.HCl Flux $(ug/cm^2/8\ hrs)$ |
| --- | --- |
| 25% $C_{12}OH$ in 2-Pyrrolidone | 2511 |
| 25% $C_{12}OH$ in 1-Methyl-2-pyrrolidone | 4552 |
| 25% $C_{12}OH$ in 1-Ethyl-2-pyrrolidone | 2841 |
| 25% $C_{12}OH$ in 1-Butyl-2-pyrrolidone | 2029 |
| 25% $C_{12}OH$ in 1,5-Dimethyl-2-pyrrolidone | 1533 |
| 25% $C_{12}OH$ in 1-Methyl-2-piperidone | 4031 |
| 25% $C_{12}OH$ in 1-Methyl-caprolactam | 2693 |

EXAMPLE 3

This sample shows the relative MCP.HCl flux with lower concentrations of $C_{12}OH$ in MP compared to the flux with 25% $C_{12}OH$ in MP.

| Combination | Relative Flux | |
| --- | --- | --- |
| 25% $C_{12}OH$ in MP | as | 1.0 |
| 10% $C_{12}OH$ in MP | | 1.0 |
| 5% $C_{12}OH$ in MP | | 0.7 |
| 1% $C_{12}OH$ in MP | | 0.6 |
| 0% $C_{12}OH$ in MP (MP alone) | | 0.1 |

EXAMPLE 4

This example shows the use of MP as a solvent in combination with various esters as adjuvants and also with myristyl myristate (solid at 38° C.) as a comparison study.

| Combination | MCP.HCl Flux$(ug/cm^2/8\ hrs)$ |
| --- | --- |
| 25% Ethyl Caprylate in MP | 2793 |
| 25% Decyl Oleate in MP | 2678 |
| 25% Myristyl Myristate in MP | 117 a |

EXAMPLE 5

This example shows comparisons of the relative flux of MCP (free base) and its HCl salt with 25% $C_{12}OH$ in MP and with 25% isopropyl myristate in MP.

| Formulation | | Relative Flux | |
| --- | --- | --- | --- |
| 25% 1-Dodecanol in MP | Free Base | as | 1.0 |
| | HCl Salt | | 1.3 |
| 25% isopropyl myristate in MP | Free Base | | 1.0 |
| | HCl Salt | | 1.2 |

EXAMPLE 6

This example shows the effect of increasing the MCP HCl concentration in a 25% $C_{12}OH$ in MP combination on MCP HCl flux. Flux increases linearly with increasing drug concentration as shown in the FIGURE.

EXAMPLE 7

This example shows the moderating effect of a diol on the system 25% $C_{12}OH$ in MP and the system 25% decyl oleate in MP.

| Formulation | Relative Flux | |
| --- | --- | --- |
| 25% $C_{12}OH$ in MP | as | 1.00 |
| 25% $C_{12}OH$ in a 1/1 volume mixture of MP/1,2-Propanediol | | 0.30 |
| 25% Decyl Oleate in MP | as | 1.00 |
| 25% Decyl Oleate in a 1/1 volume mixture of MP/1,2-Propanediol | | 0.25 |

EXAMPLE 8

This example shows the MCP. HCl flux with various concentrations of $C_{12}OH$ in a 1:1 volume mixture of MP : 1,2-propanediol.

| Formulation | Relative Flux |
| --- | --- |
| $C_{12}OH$ alone | 0.1 |
| 75% $C_{12}OH$ in MP/1,2-Propanediol | 1.7 |

| Formulation | Relative Flux |
|---|---|
| 50% $C_{12}OH$ in MP/1,2-Propanediol | 1.3 |
| 25% $C_{12}OH$ in MP/1,2-Propanediol | as 1.0 |
| 10% $C_{12}OH$ in MP/1,2-Propanediol | 1.0 |
| MP/1,2-Propanediol alone | 0.0 |

EXAMPLE 9

This example shows the moderating effect of a diol on the system 25% $C_{12}OH$ in MP along with 2.23 weight percent of MCP (free base).

| Formulation | Relative Flux |
|---|---|
| 25% $C_{12}OH$ in MP | as 1.00 |
| 25% $C_{12}OH$ in MP/2,3-Butanediol = 1/1 | 0.35 |
| 25% $C_{12}OH$ in 2,3-Butanediol | 0.05 |

EXAMPLE 10

500 mg of MCP.HCl was dissolved in 20 ml of 10% $C_{12}OH$ in MP. A 5 ml sample of the solution was added to 300 mg of hydroxy propyl cellulose (Klucel HF, Hercules Inc.) and to 300 mg of hydroxy ethyl cellulose (Natrosol 250H, Hercules Inc.). Uniform gel formulations were obtained. These formulations were added to diffusion cells and the MCP.HCl flux for 8 hours was measured.

| Formulation | MCP.HCl Flux(ug/$cm^2$/8 hrs) |
|---|---|
| Hydroxy ethyl cellulose | 1296 |
| Hydroxy propyl cellulose | 843 |

EXAMPLE 11

This control study shows the in vivo MCP.HCl plasma level in a rhesus monkey after oral administration of MCP.HCl (Reglan Tab., A.H. Robins Co.) and intravenous injection thereof (Reglan Injectable, A.H. Robins Co.).

| 20 mg Oral Administration | | | | | | | | |
|---|---|---|---|---|---|---|---|---|
| Time after application | 30' | 1 hr | 2 hrs | 3 hrs | 5 hrs | 7 hrs | | |
| MCP.HCl plasma level (ng/ml) | 8 | 19 | 7 | 5 | 5 | 3 | | |
| Intravenous Injection | | | | | | | | |
| Time after application | 10' | 20' | 40' | 60' | 90' | 2 hrs | 3 hrs | 5 hrs | 7 hrs |
| Plasma level (ng/ml) 5 mg injec. | 169 | 122 | 117 | 87 | 65 | 61 | 32 | 17 | 10 |
| 10 mg injec. | 378 | 162 | 193 | — | 148 | 93 | 45 | 40 | 28 |

EXAMPLE 12

This example shows the in vivo MCP.HCl plasma level in a rhesus monkey resulting from the use of a topical gel formulation of MCP.HCl as described below. 150 mg of MCP.HCl was dissolved in 3 ml of $C_{12}OH$ in MP. To this solution was added 90 mg of Klucel (type HF). A uniform gel was obtained. 0.5 ml of the gel was placed in a polyester cup having 4 $cm^2$ opening and a volume of 0.5 ml. The gel in the cup was applied on the monkey chest as earlier described.

| Time after application | 1 hr | 3 hrs | 7 hrs |
|---|---|---|---|
| Plasma level (ng/ml) | 117 | 65 | 72 |

EXAMPLE 13

This example shows the in vivo MCP.HCl plasma level obtained in a rhesus monkey with a topical gel formulation as described below. 200 mg of MCP.HCl was dissolved in 4 ml of 25% decyl oleate in MP. To this solution was added 160 mg of Klucel (type HF) and the system was stirred thoroughly to obtain a uniform gel. 1.0 ml of the gel was applied to a 49 $cm^2$ chest area of a rhesus monkey and the applied area was open to the air for the duration of the experiment.

| (ng/ml of Plasma) | | | | |
|---|---|---|---|---|
| 1 hr | 2 hrs | 3 hrs | 5 hrs | 7 hrs |
| 5 | 13 | 23 | 32 | 22 |

EXAMPLE 14

200 mg MCP.HCl was dissolved in 4 ml of 25% $C_{12}OH$ in 1/1 volume mixture of MP/1,2-propanediol. To this solution was added 1.2 g of polyvinyl pyrrolidone K-90 (molecular weight: 36,000) and the system stirred to obtain a viscous solution. 0.5 ml of this solution was placed in a polyester cup having a 4 $cm^2$ opening and a volume of 0.5 ml. The solution in the cup was applied to the chest of a rhesus monkey and attached thereto with adhesive.

| (ng/ml of Plasma) | | |
|---|---|---|
| 1 hr | 3 hrs | 7 hrs |
| 5 | 10 | 20 |

EXAMPLE 15

200 mg of MCP.HCl was dissolved in 4 ml of 10% $C_{12}OH$ in a 1/1 volume mixture of MP/1,2-propanediol. To this solution was added 160 mg of Klucel and the system stirred to obtain a uniform gel. 1.0 ml of the gel was applied to a 49 $cm^2$ area on the rhesus monkey chest and the applied area was left open to the air.

| (ng/ml of Plasma) | | | | |
|---|---|---|---|---|
| 1 hr | 2 hrs | 3 hrs | 5 hrs | 7 hrs |
| 75 | 146 | 178 | 121 | 93 |

What is claimed is:

1. A method of percutaneously administering metoclopramide to a mammal which comprises applying to the skin of the mammal metoclopramide in a carrier system which comprises at least one member selected from the group consisting of a monovalent alcohol ester of an aliphatic monocarboxylic acid having 8 to 32 carbon atoms, an aliphatic monoalcohol having 6 to 24 carbon atoms, and mixtures thereof, at least one member selected from the group consisting of compounds of the formula:

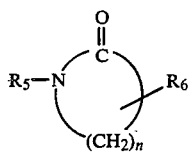

where $R_5$ is H or a $C_1$–$C_4$ alkyl group, $R_6$ is a $C_1$–$C_4$ alkyl group and n is 3, 4 or 5, wherein the esters, alcohols and compounds of the formula have a melting point below 38° C. and a $C_3$–$C_6$ diol.

2. The method of claim 1 wherein the amount of at least one ester, alcohol or mixture thereof is from 0.5 to 95% by weight based on the total weight of ester, alcohol or mixture thereof, at least one compound of the formula and metoclopramide and the amount of at least one compound of the formula is from 99.5 to 5% by weight, same basis.

3. The method of claim 2 wherein the amount of metoclopramide is from 0.1 to 60% by weight based on the weight of at least one ester, alcohol or mixture thereof and at least one compound of the formula.

4. The method of claim 3, wherein the diol is present in an amount of about 10 to about 400 wt % based on the weight of the at least one member selected from the group consisting of compounds of the formula.

5. The method of claim 4, wherein the at least one member selected from the group consisting of compounds of the formula is selected from the group consisting of 2-pyrrolidone, N-methylpyrrolidone, N-methylpiperidone, caprolactam and N-methylcaprolactam.

6. The method of claim 4, wherein the at least one member selected from the group consisting of compounds of the formula is N-methyl-2-pyrrolidone.

7. The method of claim 6, wherein the monovalent alcohol ester of an aliphatic monocarboxylic acid is selected from the group consisting of methyl laurate, ethyl laurate, butyl laurate, isopropyl myristate, decyl oleate, myristyl acetate and cetyl acetate.

8. The method of claim 4, wherein the carrier system comprises the at least one monovalent alcohol ester of an aliphatic monocarboxylic acid.

9. The method of claim 4, wherein the carrier system comprises the at least one aliphatic monoalcohol.

10. The method of claim 4, wherein the carrier system comprises 1-methyl-2-pyrrolidone, 1-dodecanol and the diol.

* * * * *